United States Patent
Dulebohn et al.

(10) Patent No.: US 6,730,518 B1
(45) Date of Patent: May 4, 2004

(54) METHOD FOR PREVENTING PHOTOOXIDATION OR AIR OXIDATION IN FOOD, PHARMACEUTICALS AND PLASTICS

(75) Inventors: Joel I. Dulebohn, Lansing, MI (US); Ronald J. Carlotti, Grand Rapids, MI (US)

(73) Assignee: Natura, Inc., Lansing, MI (US)

( * ) Notice: Subject to any disclaimer, the term of this patent is extended or adjusted under 35 U.S.C. 154(b) by 0 days.

(21) Appl. No.: 09/669,418

(22) Filed: Sep. 25, 2000

Related U.S. Application Data

(60) Provisional application No. 60/156,130, filed on Sep. 27, 1999.

(51) Int. Cl.⁷ .......................... C12P 13/04; G01N 33/02; A61K 33/30

(52) U.S. Cl. .......................... 436/90; 562/400; 562/433; 435/109; 435/110; 435/113; 435/114; 435/115; 423/635; 423/622

(58) Field of Search .......................... 436/90; 435/109, 435/110, 114, 115, 107, 108, 113, 116; 562/400, 433; 423/635, 622

Primary Examiner—Christopher S. F. Low
Assistant Examiner—Chih-Min Kam
(74) Attorney, Agent, or Firm—Foley & Lardner LLP

(57) ABSTRACT

Disclosed is a method of reducing photooxidation or air oxidation in susceptible materials such as food, plastics or pharmaceuticals comprising mixing the material with an antioxidation composition comprising at least one amino acid, at least one metal ion, and at least one carboxylic acid in an amount effective to reduce photooxidation in the material.

20 Claims, No Drawings

METHOD FOR PREVENTING PHOTOOXIDATION OR AIR OXIDATION IN FOOD, PHARMACEUTICALS AND PLASTICS

CROSS-REFERENCE TO RELATED APPLICATIONS

This application claims priority over provisional patent application U.S. Ser. No. 60/156,130, filed Sep. 27, 1999.

STATEMENT REGARDING FEDERALLY SPONSORED RESEARCH OR DEVELOPMENT

Not applicable.

BACKGROUND OF THE INVENTION

Milk, chocolate, butter, and other foods, when exposed to light, such as sunlight or fluorescent light, may develop a characteristic off-flavor caused by photooxidation or air oxidation. This tendency to develop an off-flavor significantly reduces the shelf-life of foods susceptible to photooxidation or air oxidation. Photooxidation or air oxidation can also cause plastics to develop undesired characteristics over time, and reduce the stability of pharmaceuticals.

There is a need in the food, plastics, and pharmaceutical industries for a method of reducing photooxidation or air oxidation in susceptible materials.

BRIEF SUMMARY OF THE INVENTION

The present invention includes a method for reducing photooxidation or air oxidation in susceptible materials, such as foods, plastics, and pharmaceuticals, comprising the step of mixing with the material an anti-photooxidation composition comprising at least one amino acid and at least one metal ion, the composition added in an amount sufficient to reduce photooxidation or air relative to a photooxidation or air oxidation-susceptible material lacking the anti-photooxidation composition. Preferably, the anti-photooxidation composition further comprises at least one organic acid.

Other features, objects and advantages of the present invention will become apparent to one of skill in the art after review of the specification and claims.

BRIEF DESCRIPTION OF THE SEVERAL VIEWS OF THE DRAWINGS

Not applicable.

DETAILED DESCRIPTION OF THE INVENTION

As described in the examples below, adding an antioxidation composition comprising a carboxylic acid, a metal ion, and a compound comprising an amino acid or an amino acid moiety (hereinafter referred to as an "amino acid compound" to products, such as foods, plastics and pharmaceuticals (preferably milk or white chocolate), prevents the formation of an off flavor caused by photooxidation or air oxidation of these foods.

By an "amino acid compound" it is meant an amino acid, polypeptide or protein.

By "antioxidation composition" as it is used herein, it is meant a composition that reduces the adverse effects of photooxidation or air oxidation when incorporated into a material that is susceptible to photooxidation or air oxidation.

In another embodiment, an antioxidant composition comprising an amino acid compound and a metal oxide, such as aspartate and MgO, which are capable of forming a light-absorbing complex, is used to prevent photooxidation or air oxidation in a food or other material susceptible to such oxidation. An example of a composition having at least one metal ion and at least one amino acid that we predict will be suitable for preventing photooxidation or air oxidation is provided below.

The examples below show that the method of the invention prevents photooxidation and air oxidation in foods susceptible to such oxidation. We expect that the method of the invention can also be used in pharmaceuticals and plastic to prevent the adverse effects caused by these types of oxidation.

As described in the examples below, the amino acid compound, carboxylic acid and metal ion may be formulated as an antioxidation composition that is added to photooxidation or air oxidation susceptible material. One of ordinary skill in the art would appreciate that although these components may most conveniently be added as a stabilizing composition, one could also add these components separately to the susceptible material.

In the examples below, lysine was used as the amino acid to promote prevent photooxidation or air oxidation. It is expected that either D-lysine or L-lysine may be used in the practice of the present invention. It is also expected that any amino acid may be used in the practice of the invention. It is reasonably expected that polypeptides and proteins may also be used together with a metal ion, or a metal ion and a carboxylic acid, to prevent photooxidation or air oxidation.

Malic acid and citric acid were used in the examples below to prevent photooxidation or air oxidation. It is expected that other carboxylic acids including mono, dl, tri, and polycarboxylic acids may work equally well. It Is also expected that carboxylic acids containing additional functional groups such as $NH_2^-$, $OH^-$, $PO_4^-$, and $SO_4^{-2}$ would work as well.

In the examples, below magnesium, magnesium and calcium, or magnesium, calcium and zinc were tested and were found to be suitable metal ions in the practice of the present invention. Other metal ions are expected to work as well, including group IA, group IIA, Ti, V, Cr, Mn, Co, Ni, Cu, Zn, Se, Fe, Mo, Sn, and Au.

The molar ratio of the metal ion to amino acid compound to carboxylic acid may vary depending upon the application. The molar ratio of the amino acid compound to the metal ion may vary from about 0.01 to about 20 when the amino acid compound is an amino acid monomer. The carboxylic acid to metal ion molar ratio can vary from about 0.01 to about 20. Preferably the molar ratio of the amino acid to metal ion varies from about 0.1 to about 4, and the molar ratio of carboxylic acid to metal ion varies from about 0.1 to about 4. Preferably a suitable antioxidation composition comprises at least on amino acid compound, at least one carboxylic acid and at least one metal ion, and has a pH in the range of 3 to 8.

In another embodiment of the present invention, the composition also reduces color fading in materials selected from the group consisting of food, plastics, flowers and paper. One cause of color fading is due to UV light interaction with the dyes and pigments comprising functional groups such as alcohol, ester, aldehyde, ketones, ether, and carboxylic acid resulting in breakdown of the dye and pigment color. The compositions of amino acid, metal and organic acid can reduce and/or prevent the breakdown of dye or pigment color by two methods. In one method, the composition adsorbs UV light that can interact with the dye and pigment and emit white light. This absorption will prevent the UV light from interaction with the functional groups of the dyes or pigments. In the second method, the functional groups and metals of the composition can stabilize the functional groups of the dyes and pigment by forming chelated bonds and/or hydrogen bonds. This will help prevent UV light from breaking down the dyes and pigments.

The composition can be blended or applied to the surface of a product, such as food, plastic flowers, and paper, to reduce and/or prevent the UV light from interacting with the dyes and pigments. We usually observed that the fading of the material comprising the composition of amino acid, metal and organic acid to be less than the fading of untreated material without the composition.

In another embodiment of the present invention, the composition also reduces degradation of a substance selected from the group consisting of caffeine, vitamins (preferably pyridoxine, riboflavin, vitamin D, niacin, phylloquinone), folic acid, isoflavones, licorice, ginkgo, garlic, beta-carotene, peppermint, herbal extract, botanicals, peppermint, herbal extract, botanicals, natural and artificial flavors. The materials described above have functional groups such as alcohol, ester, aldehyde, ketones, ether, and carboxylic acid, that can interact with metal and functional groups of the composition of amino acid, metal and organic acid. Some of the interaction are hydrogen bonding and chelation. Drinks were prepared with vitamins and flavor with and without the composition of amino acid, metal and organic acid. The drinks were pasteurized. The drinks were then taste tested, and the drinks with the composition had an overall better taste.

In preferred embodiment, the product is milk or white chocolate and the level of the composition is between 0.001% and 2% w/w (Note: all percentage concentrations are w/w).

In a most preferred embodiment, the product is milk, the range is 0.01% to 0.5%, and the composition is 65% solid solution of lysine:magnesium:malic acid:citric acid with a molar ratio of 1.49:1:2.16:0.72.

In another embodiment, the product is white chocolate, the range is from 0.1% to 0.5%, and the composition is lysine:calcium:malic acid:citric acid with a molar ratio of 1.49:1:2.16:0.72, which is a crème.

The following non-limiting examples are intended to be purely illustrative.

EXAMPLES

Preparation of Antioxidation Compositions

The following are examples of antioxidation compositions that may be used to protect products, such as food, pharmaceuticals, and plastics, against photooxidation or air oxidation.

Composition A
 160 g water
 110 g lysine HOH (0.67 moles)
 40 g MgO (0.99 moles)
 130 g malic acid (0.97 moles)
 62 g citric acid (0.32 moles)
The pH of the solution varies from 4.4 to 4.8 and is approximately 65% solid solution.

Composition B
 157 g water
 110 g lysine HOH (0.67 moles)
 10 g CaO (0.18 moles)
 18 g MgO (0.45 moles)
 100 g malic acid (0.75 moles)
 73 g citric acid (0.38 moles)
The pH of the solution varies from 3.9 to 4.3 and is approximately 65% solid solution.

Composition C
 166.4 g water
 143 g lysine HOH (0.87 moles)
 13 g CaO (0.23 moles)
 13 g MgO (0.32 moles)
 13 g ZnO (0.16 moles)
 122.2 g malic acid (0.91 moles)
 58.5 g citric acid (0.30 moles)
The pH of the solution varies from 4.2 to 4.6 and is approximately 65% solid solution.

Composition D
 1571.5 g water
 1155.1 g lysine HOH (7.03 moles)
 189.1 g MgO (4.69 moles)
 1365.1 g malic acid (10.18 moles)
 654.6 g citric acid (3.41 moles)
The pH of the solution varies from 3.6 to 4.0 and is approximately 65% solid solution.

Composition E
 10 g water
 10 g lysine HOH (0.061 moles)
 40 g MgO (0.060 moles)
 7.2 g succinic acid (0.061 moles)
The pH of the solution varies from 8 to 9.

Composition F
 15 g water
 8.2 g DL-aspartic acid (0.062 moles)
 2.5 g MgO (0.062 moles)

Compositions A–F may be used as a liquid as prepared, or may be used as a solid after drying by any suitable means, including, for example, microwave, spray dried, drum dried, and any other feasible process, such as fluid bed agglomeration and cooker extrusion.

Evaluation of Milk Stability After Exposure to Light

The following samples were prepared, exposed to light and evaluated as described below.

Control
A 200-ml aliquot of whole milk in a clear container wrapped in aluminum foil.

Sample 1
A 200-ml aliquot of whole milk in a clear container.

Sample 2
A 200-ml aliquot of whole milk and 2 grams of composition B.

The control and test samples were exposed for two hours and 10 minutes to a Sylvania Superflood light (blue bulb) placed at a distance of 11 inches from the container. The control and test samples were evaluated by tasting.

No off-flavor was noted in the control. Sample one had an off taste, similar to that of sour milk. Sample two tasted comparable to the control.

Evaluation of White Chocolate Stability After Exposure to Light

The following samples were prepared, exposed to fluorescent light and evaluated as described below.

Control

White chocolate not exposed to light

Sample 1

White chocolate exposed to light

Sample 2

White chocolate blended with composition A (0.2% w/w) and exposed to light

Sample 3

White chocolate blended with composition B (0.2% w/w) and exposed to light

Sample 4

White chocolate blended with composition C (0.2% w/w) and exposed to light

Sample 5

White chocolate blended with composition D (0.2% w/w) and exposed to light

Each sample was exposed to light for several hours to days and sampled periodically for taste tests. The chocolate comprising anti-photooxidation composition A, B, C, or D had a flavor comparable to the control, whereas the untreated white chocolate (sample A) had an off flavor. Sample C, which comprises composition B, had a flavor closest to the control.

We claim:

1. A method of reducing photooxidation or air oxidation in a food product comprising the step of dispersing within the food product an antioxidation composition comprising a mixture of the following components:
   (a) one or more amino acids selected from the group consisting of lysine and aspartic acid;
   (b) one or more metal oxides selected from the group consisting of CaO, MgO and ZnO; and
   (c) one or more organic acids selected from the group consisting of malic acid, citric acid and succinic acid;
   wherein the antioxidation composition is added in an amount between 0.001% and 2% (w/w) of the food product, and the food product includes an amount of the antioxidation composition, which is effective to reduce photooxidation or air oxidation of the food product.

2. The method of claim 1, wherein the molar ratio of the amino acid to metal oxide is between 0.01 and 20.

3. The method of claim 1, wherein the molar ratio of organic acid to metal oxide is between 0.01 and 20.

4. The method of claim 2, wherein the molar ratio of the amino acid to metal oxide is between 0.1 and 4.

5. The method of claim 2, wherein the molar ratio of organic acid to metal oxide is between 0.1 and 4.

6. The method of claim 1, wherein the food product is milk.

7. The method of claim 6, wherein the food product includes 0.01% to 1.0% (w/w) of the antioxidation composition.

8. The method of claim 1, wherein the food product is white chocolate.

9. The method of claim 8, wherein the food product includes 0.1% to 0.5% (w/w) of the antioxidation composition.

10. The method of claim 6, wherein the food product includes 0.01% to 2.0% (w/w) of the antioxidation composition.

11. The method of claim 9, wherein the antioxidation composition comprises lysine:calcium oxide:malic acid:citric acid with a molar ratio of 1.49:1:2.16:0.72.

12. A method of reducing photooxidation or air oxidation in a food product comprising the step of dispersing within the food product an antioxidation composition, wherein the antioxidation composition is formed from a mixture comprising the following components:
   (a) one or more amino acids selected from the group consisting of lysine and aspartic acid;
   (b) one or more metal oxides selected from the group consisting of CaO, MgO and ZnO; and
   (c) one or more organic acids selected from the group consisting of malic acid, citric acid and succinic acid;
   wherein the antioxidation composition is added in an amount from 0.001% to 2% (w/w) of the food product, and the food product includes an amount of the antioxidation composition, which is effective to reduce photooxidation or air oxidation of the food product.

13. The method of clam 12, wherein the mixture includes the amino acid and the metal oxide in a molar ratio of 0.01 to 20.

14. The method of claim 12, wherein the mixture includes the organic acid and the metal oxide in a molar ratio of 0.01 to 20.

15. The method of claim 12, wherein the mixture includes the amino acid and the metal oxide in a molar ratio of 0.1 to 4.

16. The method of claim 12, wherein the mixture includes the organic acid and the metal oxide in a molar ratio of 0.1 to 4.

17. The method of claim 12, wherein the food product is milk.

18. The method of claim 12, wherein the food product is white chocolate.

19. The method of claim 12, wherein the food product includes 0.01% to 2.0% (w/w) of the antioxidation composition.

20. The method of claim 12, wherein the antioxidation composition is a 65% (w/w) aqueous solution formed from a mixture comprising lysine:magnesium oxide:malic acid:citric acid with a molar ratio of 1.49:1:2.16:0.72.

* * * * *